United States Patent
Khurram et al.

(10) Patent No.: US 11,286,220 B2
(45) Date of Patent: Mar. 29, 2022

(54) PROCESS FOR 1-BUTENE PRODUCTION FROM N-BUTANE DEHYDROGENATION THROUGH EFFICIENT DOWNSTREAM SEPARATIONS

(71) Applicant: SABIC Global Technologies B.V., Bergen op Zoom (NL)

(72) Inventors: Shehzada Khurram, Riyadh (SA); Muhammad H. Haider, Riyadh (SA); Waleed Al-Dahlous, Riyadh (SA)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 0 days.

(21) Appl. No.: 17/283,040

(22) PCT Filed: Aug. 27, 2019

(86) PCT No.: PCT/IB2019/057210
§ 371 (c)(1),
(2) Date: Apr. 6, 2021

(87) PCT Pub. No.: WO2020/074974
PCT Pub. Date: Apr. 16, 2020

(65) Prior Publication Data
US 2021/0380504 A1    Dec. 9, 2021

Related U.S. Application Data

(60) Provisional application No. 62/743,479, filed on Oct. 9, 2018.

(51) Int. Cl.
*C07C 7/00*    (2006.01)
*C07C 7/04*    (2006.01)
(Continued)

(52) U.S. Cl.
CPC ............. *C07C 7/005* (2013.01); *B01D 3/145* (2013.01); *B01D 3/322* (2013.01); *C07C 5/2506* (2013.01);
(Continued)

(58) Field of Classification Search
CPC .. C07C 7/00; C07C 7/04; C07C 7/144; C07C 5/333; C07C 5/25; B01D 3/14; B01D 3/32
See application file for complete search history.

(56) References Cited

U.S. PATENT DOCUMENTS 2,362,218 A * 11/1944 Schulze et al. ....... C07C 11/167
585/326
2,415,921 A    2/1947 Wagner
(Continued)

FOREIGN PATENT DOCUMENTS

CN    1708466 A    12/2005
CN    1990437 A    7/2007
(Continued)

OTHER PUBLICATIONS

Gehre et al. "Sustainable Separations of $C_4$-Hydrocarbons by Using Microporous Materials." *ChemSusChem*, 10 (2017) 3947-3963.
(Continued)

*Primary Examiner* — Youngsul Jeong
(74) *Attorney, Agent, or Firm* — Norton Rose Fulbright US LLP

(57) ABSTRACT

System and method for producing 1-butene are disclosed. The method includes dehydrogenating butane to form a mixture comprising butene isomers. 1-butene is separated from the mixture using a system that includes a membrane. The system also includes an isomerizing unit for isomerizing cis-2-butene and trans-2-butene to form additional 1-butene.

20 Claims, 2 Drawing Sheets

(51) Int. Cl.
*C07C 7/14* (2006.01)
*B01D 3/14* (2006.01)
*C07C 7/144* (2006.01)
*C07C 5/333* (2006.01)
*B01D 3/32* (2006.01)
*C07C 5/25* (2006.01)
*B01D 71/02* (2006.01)

(52) U.S. Cl.
CPC .......... *C07C 5/3335* (2013.01); *C07C 5/3337* (2013.01); *C07C 7/04* (2013.01); *C07C 7/144* (2013.01); *B01D 71/028* (2013.01); *C07C 2523/06* (2013.01); *C07C 2523/42* (2013.01); *C07C 2523/60* (2013.01)

(56) References Cited

U.S. PATENT DOCUMENTS

| | | | |
|---|---|---|---|
| 5,563,299 | A | 10/1996 | Paludetto et al. |
| 9,272,262 | B2 | 3/2016 | Polshettiwar et al. |
| 2007/0055088 | A1 | 3/2007 | Schindler et al. |
| 2007/0161841 | A1* | 7/2007 | Schindler .................. C07C 5/05 585/658 |
| 2007/0161842 | A1 | 7/2007 | Johann et al. |
| 2008/0183024 | A1* | 7/2008 | Klanner ................ C07C 5/3337 585/633 |
| 2009/0200236 | A1 | 8/2009 | Diefenbacher et al. |
| 2013/0152789 | A1 | 6/2013 | Polshettiwar et al. |
| 2015/0038758 | A1 | 2/2015 | Park et al. |

FOREIGN PATENT DOCUMENTS

| | | |
|---|---|---|
| CN | 101489959 A | 7/2009 |
| DE | 3417549 A1 | 11/1985 |
| DE | 102004001974 A1 | 8/2005 |
| JP | H0692876 A | 4/1994 |
| RU | 2436758 C2 | 8/2011 |
| TW | 200523239 A | 7/2005 |
| WO | WO2005063656 A1 | 7/2005 |
| WO | WO2008006879 A1 | 1/2008 |
| WO | WO2014053431 A2 | 4/2014 |
| WO | WO2014192020 A2 | 12/2014 |

OTHER PUBLICATIONS

International Search Report and Written Opinion from PCT/IB2019/057210 dated Nov. 12, 2019, 11 pages.

* cited by examiner and# PROCESS FOR 1-BUTENE PRODUCTION FROM N-BUTANE DEHYDROGENATION THROUGH EFFICIENT DOWNSTREAM SEPARATIONS

CROSS REFERENCE TO RELATED APPLICATIONS

This application is a national phase application under 35 U.S.C. § 371 of International Application No. PCT/IB2019/057210 filed Aug. 27, 2019, which claims priority to U.S. Provisional Patent Application No. 62/743,479 filed Oct. 9, 2018. The entire contents of each of the above-referenced disclosures is specifically incorporated by reference herein without disclaimer.

FIELD OF INVENTION

The present invention generally relates to the production of 1-butene. More specifically, the present invention relates to dehydrogenating n-butane to form a mixture comprising butene isomers and recovering 1-butene from the mixture.

BACKGROUND OF THE INVENTION

1-Butene is normally used as a comonomer in polyethylene production. One method of producing 1-butene is separating it from C4 refinery streams. These C4 refinery streams are formed during steam cracking or fluid catalytic cracking of hydrocarbon feed to produce ethylene. 1-Butene is also produced by dehydrogenating n-butane to form isomers of butene, including 1-butene, and one or more of iso-butene, trans-2-butene, and cis-2-butene. After the dehydrogenating, the 1-butene is separated from the other isomers. In production processes that involve the dehydrogenation of n-butane to form butenes, the separation of 1-butene from the other butene isomers is a major hurdle to overcome, if a high quality 1-butene product is to be achieved.

Separating 1-butene from other butene isomers is very challenging because these materials all have boiling points that are close. Hence, traditional separation techniques, such as distillation, are relatively ineffective. Further, conversion rates of n-butane to 1-butene, in these processes are relatively low, so it is difficult to achieve suitable production capacity for 1-butene in existing refineries.

BRIEF SUMMARY OF THE INVENTION

With the above described issues associated with the production of 1-butene in mind, a process has been developed that can achieve required 1-butene production capacity at the desired purity. In this process, n-butane is dehydrogenated to form a mixture comprising butene isomers and unreacted n-butane. The mixture is separated and unreacted n-butane from this separation process can be sent back as recycle to be dehydrogenated. Iso-butene and 1-butene recovered from the separation process are routed to a membrane to separate the iso-butene from 1-butene. A mixture of trans-2-butene and cis-2-butene from the separation process can be used as feedstock for an isomerization unit. In this isomerization unit, both trans-2-butene and cis-2-butene are converted to 1-butene.

Embodiments of the invention include a method of producing 1-butene. The method includes dehydrogenating n-butane to produce a first stream comprising 1-butene, isobutene, trans-2-butene, cis-2-butene, and n-butane. The method further includes distilling, in a distillation column, the first stream to produce a second stream comprising primarily 1-butene and isobutene, collectively and a third stream comprising primarily trans-2-butene and cis-2-butene, collectively. Further yet, the method includes separating the second stream to produce a fourth stream comprising primarily 1-butene and a fifth stream comprising primarily isobutene.

Embodiments of the invention include a method of producing 1-butene. The method includes dehydrogenating n-butane to produce a first stream comprising 1-butene, isobutene, trans-2-butene, cis-2-butene, and n-butane. The method further includes distilling, in a distillation column, the first stream to produce a second stream comprising primarily 1-butene and isobutene, collectively, and a third stream comprising primarily trans-2-butene and cis-2-butene, collectively. Further yet, the method includes separating the second stream into a fourth stream comprising primarily 1-butene and a fifth stream comprising primarily isobutene. The separating of the second stream is performed with a membrane. The method also includes withdrawing a sixth stream from the distillation column, where the sixth stream comprises primarily n-butane.

The following includes definitions of various terms and phrases used throughout this specification.

The terms "about" or "approximately" are defined as being close to as understood by one of ordinary skill in the art. In one non-limiting embodiment the terms are defined to be within 10%, preferably, within 5%, more preferably, within 1%, and most preferably, within 0.5%.

The terms "wt. %", "vol. %" or "mol. %" refer to a weight, volume, or molar percentage of a component, respectively, based on the total weight, the total volume, or the total moles of material that includes the component. In a non-limiting example, 10 moles of component in 100 moles of the material is 10 mol. % of component.

The term "substantially" and its variations are defined to include ranges within 10%, within 5%, within 1%, or within 0.5%.

The terms "inhibiting" or "reducing" or "preventing" or "avoiding" or any variation of these terms, when used in the claims and/or the specification, include any measurable decrease or complete inhibition to achieve a desired result.

The term "effective," as that term is used in the specification and/or claims, means adequate to accomplish a desired, expected, or intended result.

The use of the words "a" or "an" when used in conjunction with the term "comprising," "including," "containing," or "having" in the claims or the specification may mean "one," but it is also consistent with the meaning of "one or more," "at least one," and "one or more than one."

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process of the present invention can "comprise," "consist essentially of," or "consist of" particular ingredients, components, compositions, etc., disclosed throughout the specification.

The term "primarily," as that term is used in the specification and/or claims, means greater than any of 50 wt. %, 50 mol. %, and 50 vol. %. For example, "primarily" may include 50.1 wt. % to 100 wt. % and all values and ranges there between, 50.1 mol. % to 100 mol. % and all values and ranges there between, or 50.1 vol. % to 100 vol. % and all values and ranges there between.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

For a more complete understanding, reference is now made to the following descriptions taken in conjunction with the accompanying drawings, in which.

DETAILED DESCRIPTION OF THE INVENTION

A method has been discovered for producing 1-butene at improved production capacity and purity as compared with conventional processes. In the discovered method, n-butane is dehydrogenated to form a mixture comprising butene isomers and unreacted n-butane. Unreacted n-butane is separated from this mixture. The unreacted n-butane from this separation process can be sent back as recycle to be dehydrogenated. Iso-butene and 1-butene recovered from the separation process is routed to a membrane to separate the iso-butene from 1-butene. A mixture of trans-2-butene and cis-2-butene from the separation process can be used as feedstock for an isomerization unit. In this isomerization unit, both trans-2-butene and cis-2-butene are converted to 1-butene.

Figure 1:
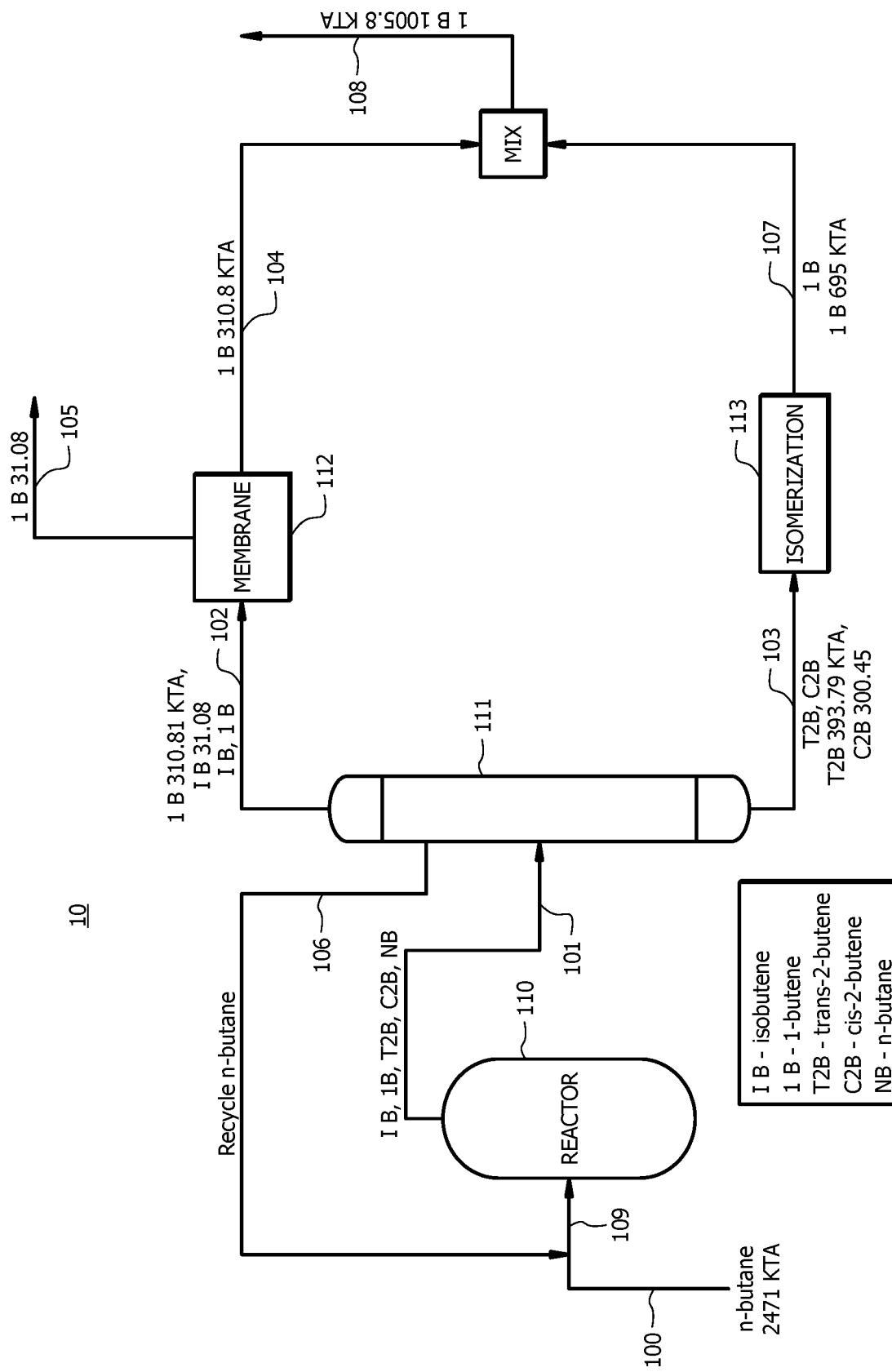
FIG. 1 is a system for producing 1-butene, according to embodiments of the invention.
Figure 2:
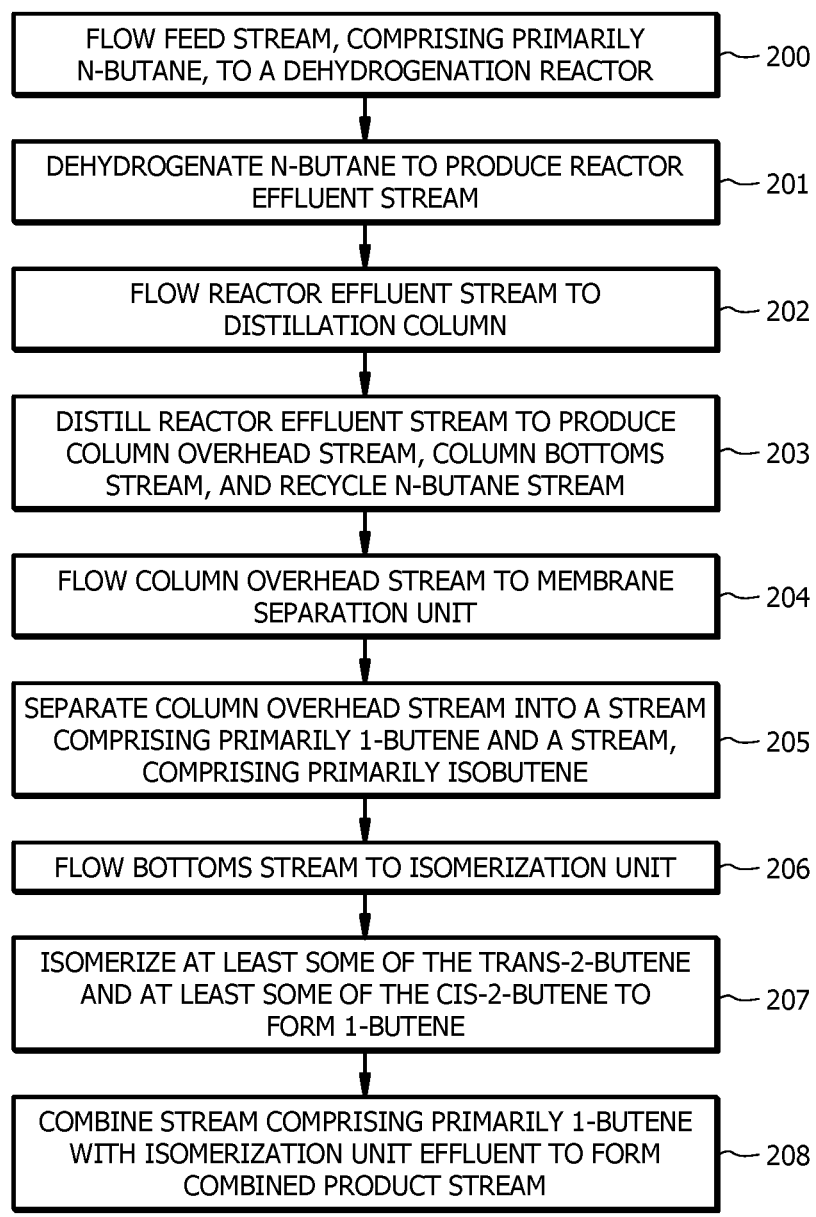
FIG. 2 is a method of producing 1-butene, according to embodiments of the invention.

FIG. 1 shows system 10 for producing 1-butene, according to embodiments of the invention. FIG. 2 shows method 20 for producing 1-butene, according to embodiments of the invention. Method 20 may be implemented with system 10. In embodiments of the invention, the mass numbers for streams shown in FIG. 1 may vary and the mass number for each stream can include mass numbers in a range from 10% less than the mass number shown to 10% greater than the mass number shown, including all ranges and values therein.

Method 20, as implemented using system 10, may include, at block 200, flowing feed stream 100, which comprises primarily n-butane, to dehydrogenation reactor 110. In embodiments of the invention, feed stream 100 may be combined with recycle n-butane stream 106 to form combined stream 109, which is flowed to dehydrogenation reactor 110. Alternatively or additionally, feed stream 100 and recycle n-butane stream 106 may be provided to dehydrogenation reactor 110 separately. According to embodiments of the invention, feed stream 100 may be sourced from different types of feedstock and may comprise 99 to 99.5 wt. % n-butane.

At block 201, method 20 may further involve dehydrogenating n-butane of feed stream 100, in dehydrogenation reactor 110, to produce reactor effluent stream 101. Reactor effluent stream 101, according to embodiments of the invention, is a mixture comprising one or more of 1-butene, isobutene, trans-2-butene, cis-2-butene, and n-butane. Dehydrogenation reactor 110, in embodiments of the invention, is operated to provide reaction conditions for feed stream 100 that includes a temperature in a range of 500 to 650° C., a pressure in a range of 0 to 10 bar, and a GHSV in a range of 1000 to 5000 $h^{-1}$. According to embodiments of the invention, reactor effluent stream 101 comprises 20 wt. % to 30 wt. % 1-butene, 2 wt. % to 5 wt. % isobutene, 25 wt. % to 35 wt. % trans-2-butene, 20 wt. % to 30 wt. % cis-2-butene, and 30 wt. % to 50 wt. % n-butane. Further, in embodiments of the invention, the dehydrogenation reaction that occurs in dehydrogenation reactor 110 may be catalyzed by a catalyst that comprises platinum and/or tin.

Method 20, according to embodiments of the invention, includes flowing reactor effluent stream 101 to distillation column 111, at block 202. Then, at block 203, in embodiments of the invention, distillation column 111 distills reactor effluent stream 101 to produce column overhead stream 102, column bottoms stream 103, and recycle n-butane stream 106. According to embodiments of the invention, the conditions for carrying out the distilling includes an overhead boiling range of −7 to 0° C., a reboiler boiling range of 1 to 5° C., and a pressure in a range of 0.01 to 1 MPa. Column overhead stream 102, in embodiments of the invention, comprises primarily 1-butene and isobutene, collectively and column bottoms stream 103 comprises primarily trans-2-butene and cis-2-butene, collectively.

At block 204, in embodiments of the invention, column overhead stream 102 is routed to membrane separation unit 112. According to embodiments of the invention, membrane separation unit 112 comprises a membrane adapted to separate hydrocarbon mixtures based on molecular sizes. In embodiments of the invention, at block 205, membrane separation unit 112 separates column overhead stream 102 into stream 104, comprising primarily 1-butene, and stream 105, comprising primarily isobutene.

According to embodiments of the invention, the membrane of membrane separation unit 112 comprises crystalline microporous materials such as one or more zeolitic imidazolate framework (ZIF). ZIFs are structurally equivalent to zeolites and/or other crystalline materials, but with different building blocks. ZIFs typically have pore sizes of less than 2 nm. Their regular pore structure enables them to differentiate gas molecules based on their molecular size. ZIFs in this technology are developed and functionalized to be effective and stable membranes for gas separations, either in powder form or in a continuous membrane form. See U.S. patent application Ser. No. 13/709,155. Preferably, column overhead stream 102 is fed to membrane separation unit 112 in a substantially gaseous phase. The separation process carried out by membrane separation unit 112 at block 205, in embodiments of the invention, can involve the separation of $C_{2-}$ hydrocarbons (e.g., hydrogen, methane, ethane, and ethylene) from $C_{3+}$ hydrocarbons (e.g., propane, propylene, butane, butylene, isobutene.).

In embodiments of the invention, stream 104 comprises 90 wt. % to 95 wt. % 1-butene and 5 wt. % to 10 wt. % isobutene. Stream 105, in embodiments of the invention, comprises 98 wt. % to 99 wt. % isobutene.

Method 20, at block 206, can include flowing column bottoms stream 103 to isomerization unit 113. According to embodiments of the invention, column bottoms stream 103 comprises 50 wt. % to 60 wt. % trans-2-butene and 40 wt. % to 50 wt. % cis-2-butene. Isomerization unit 113 is adapted to isomerize cis-2-butene and isobutene to form 1-butene. So block 207, according to embodiments of the invention, comprises isomerizing at least some of the trans-2-butene and at least some of the cis-2-butene in column bottoms stream to form 1-butene. As shown in FIG. 1, such 1-butene is comprised in isomerization unit effluent stream 107, which is flowed from isomerization unit 113, at block, 208, according to embodiments of the invention. According to embodiments of the invention, at block 207, isomerization unit 113 is operated to provide conditions for carrying out the isomerizing that includes a temperature in a range of 50 to 60° C., a pressure in a range of 0 to 5 MPa, and a space velocity in a range of 1000 to 2000 h$^{-1}$ by using positional sulfocationic exchangers. In embodiments of the invention, isomerization unit effluent stream 107 comprises 99 wt. % to 99.5 wt. % 1-butene.

According to embodiments of the invention, recycle n-butane stream 106, withdrawn from the distillation column 111, comprises primarily n-butane. Recycle n-butane stream 106 may be withdrawn, in embodiments of the invention, from a tray whose number is in a range of 98 to 99% of the total number of trays in the distillation column, wherein the trays are numbered from bottom of the distillation column upwards. For example, if there are 100 trays in distillation column 111, recycle n-butane stream 106 can be withdrawn from tray 98 or 99, counting from the bottom tray upwards. As noted above, recycle n-butane stream 106 may be recycled to dehydrogenation reactor 110 (combined with feed stream 100, separate from feed stream 100, or both) so that recycle n-butane stream 106 can be subject to dehydrogenating conditions such that at least some of the recycle n-butane stream is dehydrogenated to form butenes. In embodiments of the invention, recycle n-butane stream 106 comprises 98 wt. % to 99 wt. % n-butane.

At block 208, in embodiments of the invention, method 20 involves combining stream 104 with isomerization unit effluent stream 107 to form combined product stream 108. According to embodiments of the invention, combined product stream 108 comprises 99 wt. % to 99.8 wt. % 1-butene.

Although embodiments of the present invention have been described with reference to blocks of FIG. 2, it should be appreciated that operation of the present invention is not limited to the particular blocks and/or the particular order of the blocks illustrated in FIG. 2. Accordingly, embodiments of the invention may provide functionality as described herein using various blocks in a sequence different than that of FIG. 2.

In the context of the present invention, at least the following 19 embodiments are described. Embodiment 1 is a method of producing 1-butene. The method includes dehydrogenating n-butane to produce a first stream containing 1-butene, isobutene, trans-2-butene, cis-2-butene, and n-butane. The method further includes distilling, in a distillation column, the first stream to produce a second stream containing primarily 1-butene and isobutene, collectively and a third stream containing primarily trans-2-butene and cis-2-butene, collectively. The method also includes separating the second stream to produce a fourth stream containing primarily 1-butene and a fifth stream containing primarily isobutene. Embodiment 2 is the method of embodiment 1, wherein the separating of the second stream is performed with a membrane. Embodiment 3 is the method of either of embodiments 1 or 2, wherein the membrane contains zeolitic imidazolate framework (ZIF). Embodiment 4 is the method of any of embodiments 1 to 3, further including withdrawing a sixth stream from the distillation column, wherein the sixth stream contains primarily n-butane. Embodiment 5 is the method of any of embodiments 1 to 4, wherein the fourth stream contains 90 wt. % to 95 wt. % 1-butene and 5 wt. % to 10 wt. % isobutene. Embodiment 6 is the method of any of embodiments 1 to 5, wherein the fifth stream contains 98 wt. % to 99 wt. % isobutene. Embodiment 7 is the method of any of embodiments 1 to 6, wherein conditions for carrying out the dehydrogenating include a temperature in a range of 500 to 650° C., a pressure in a range of 0 to 10 bar, and a GHSV in a range of 1000 to 5000 h$^{-1}$. Embodiment 8 is the method of any of embodiments 1 to 7, wherein the dehydrogenating is catalyzed by a catalyst that contains platinum and/or tin. Embodiment 9 is the method of any of embodiments 1 to 8, wherein first stream contains 20 wt. % to 30 wt. % 1-butene, 2 wt. % to 5 wt. % isobutene, 25 wt. % to 35 wt. % trans-2-butene, 20 wt. % to 30 wt. % cis-2-butene, and 30 wt. % to 50 wt. % n-butane. Embodiment 10 is the method of any of embodiments 1 to 9, wherein the conditions for carrying out the distilling include an overhead boiling range of −7 to 0° C., a reboiler boiling range of 1 to 5° C., and a pressure in a range of 0.01 to 1 MPa. Embodiment 11 is the method of any of embodiments 1 to 10, wherein the sixth stream is withdrawn from a tray whose number is in a range of 98 to 99% of total number of trays in the distillation column, wherein the trays are numbered from bottom of the distillation column upwards. Embodiment 12 is the method of any of embodiments 1 to 11, wherein the sixth stream is recycled to a dehydrogenation reactor that is carrying out the dehydrogenating. Embodiment 13 is the method of any of embodiments 1 to 12, wherein the sixth stream contains 98 wt. % to 99 wt. % n-butane. Embodiment 14 is the method of any of embodiments 1 to 13, wherein the third stream contains 50 wt. % to 60 wt. % trans-2-butene and 40 wt. % to 50 wt. % cis-2-butene. Embodiment 15 is the method of any of embodiments 1 to 14, further including isomerizing, in an isomerizing unit, at least some of the trans-2-butene and at least some of the cis-2-butene in the third stream to form 1-butene that is contained in a seventh stream flowing from the isomerization unit. Embodiment 16 is the method of embodiment 15, wherein conditions for carrying out the isomerizing includes a temperature in a range of 50 to 60° C., a pressure in a range of 0 to 5 MPa, and a space velocity in a range of 1000 to 2000 h$^{-1}$. Embodiment 17 is the method of either of embodiments 15 and 16, wherein the seventh stream contains 99 wt. % to 99.8 wt. % 1-butene. Embodiment 18 is the method of any of embodiments 15 to 17, wherein the fourth stream and the seventh stream are combined to form an eighth stream. Embodiment 19 is the method of embodiment 18, wherein the eighth stream contains 99 wt. % to 99.8 wt. % 1-butene.

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods, or steps.

The invention claimed is:

1. A method of producing 1-butene, the method comprising:
    dehydrogenating n-butane to produce a first stream comprising 1-butene, isobutene, trans-2-butene, cis-2-butene, and n-butane;
    distilling, in a distillation column, the first stream to produce a second stream comprising primarily 1-butene and isobutene, collectively and a third stream comprising primarily trans-2-butene and cis-2-butene, collectively; and
    separating the second stream to produce a fourth stream comprising primarily 1-butene and a fifth stream comprising primarily isobutene.

2. The method of claim 1, wherein the separating of the second stream is performed with a membrane.

3. The method of claim 2, wherein the membrane comprises zeolitic imidazolate framework.

4. The method of claim 1, further comprising:
    withdrawing a sixth stream from the distillation column, wherein the sixth stream comprises primarily n-butane.

5. The method of claim 1, wherein the fourth stream comprises 90 wt. % to 95 wt. % 1-butene and 5 wt. % to 10 wt. % isobutene.

6. The method of claim 1, wherein the fifth stream comprises 98 wt. % to 99 wt. % isobutene.

7. The method of claim 1, wherein conditions for carrying out the dehydrogenating comprise a temperature in a range of 500 to 650° C., a pressure in a range of 0 to 10 bar, and a GHSV in a range of 1000 to 5000 h$^{-1}$.

8. The method of claim 1, wherein the dehydrogenating is catalyzed by a catalyst that comprises platinum and/or tin.

9. The method of claim 1, wherein the first stream comprises 20 wt. % to 30 wt. % 1-butene, 2 wt. % to 5 wt. % isobutene, 25 wt. % to 35 wt. % trans-2-butene, 20 wt. % to 30 wt. % cis-2-butene, and 30 wt. % to 50 wt. % n-butane.

10. The method of claim 1, wherein the distilling is conducted at an overhead boiling range of −7 to 0° C., a reboiler boiling range of 1 to 5° C., and a pressure in a range of 0.01 to 1 MPa.

11. The method of claim 4, wherein the sixth stream is withdrawn from a tray whose number is in a range of 98 to 99% of total number of trays in the distillation column, wherein the trays are numbered from bottom of the distillation column upwards.

12. The method of claim 4, wherein the sixth stream is recycled to a dehydrogenation reactor that is carrying out the dehydrogenating.

13. The method of claim 4, wherein the sixth stream comprises 98 wt. % to 99 wt. % n-butane.

14. The method of claim 1, wherein the third stream comprises 50 wt. % to 60 wt. % trans-2-butene and 40 wt. % to 50 wt. % cis-2-butene.

15. The method of claim 1, further comprising:
    isomerizing, in an isomerizing unit, at least some of the trans-2-butene and at least some of the cis-2-butene in the third stream to form 1-butene that is comprised in a seventh stream flowing from the isomerization unit.

16. The method of claim 15, wherein conditions for carrying out the isomerizing includes a temperature in a range of 50 to 60° C. and a pressure in a range of 0 to 5 MPa.

17. The method of claim 15, wherein the seventh stream comprises 99 wt. % to 99.8 wt. % 1-butene.

18. The method of claim 15, wherein the fourth stream and the seventh stream are combined to form an eighth stream.

19. The method of claim 18, wherein the eighth stream comprises 99 wt. % to 99.8 wt. % 1-butene.

20. The method of claim 16, wherein the fourth stream and the seventh stream are combined to form an eighth stream.

* * * * *